US012800566B2

(12) United States Patent
Zhou et al.

(10) Patent No.: US 12,800,566 B2
(45) Date of Patent: Nov. 17, 2026

(54) TEMPERATURE-RAINFALL-RESERVOIR WATER COMBINED TESTING SYSTEM AND METHOD FOR PERMAFROST LANDSLIDE MODEL

(71) Applicant: CHINA UNIVERSITY OF GEOSCIENCES (WUHAN), Wuhan (CN)

(72) Inventors: Jiaqing Zhou, Wuhan (CN); Hao Lu, Wuhan (CN); Changdong Li, Wuhan (CN); Hongbin Liu, Wuhan (CN); Qilong Li, Wuhan (CN)

(73) Assignee: CHINA UNIVERSITY OF GEOSCIENCES (WUHAN), Wuhan (CN)

( * ) Notice: Subject to any disclaimer, the term of this patent is extended or adjusted under 35 U.S.C. 154(b) by 259 days.

(21) Appl. No.: 18/666,845

(22) Filed: May 17, 2024

(65) Prior Publication Data

US 2025/0354974 A1 Nov. 20, 2025

(51) Int. Cl.
*G01N 33/24* (2006.01)
*G01B 11/16* (2006.01)
*G01N 15/08* (2006.01)

(52) U.S. Cl.
CPC ......... *G01N 33/246* (2013.01); *G01B 11/165* (2013.01); *G01N 15/0826* (2013.01)

(58) Field of Classification Search
None
See application file for complete search history.

(56) References Cited

U.S. PATENT DOCUMENTS 11,175,273 B1 11/2021 Zbinden
11,768,189 B2 9/2023 Brady
11,982,664 B1 5/2024 Zheng et al.
12,183,216 B1 * 12/2024 Lyu ........................ G01N 33/24
2014/0318262 A1 * 10/2014 Kia ......................... G01L 1/242
73/784
2016/0216247 A1 * 7/2016 Kong .................. G01N 1/2806

FOREIGN PATENT DOCUMENTS

CN 105510556 A * 4/2016 ............. G01N 33/24
CN 109386283 A * 2/2019 ........... E21B 49/001
CN 114019143 A * 2/2022 ............. G01N 33/24
CN 115371726 A * 11/2022 ............. G01D 21/02

* cited by examiner

*Primary Examiner* — Mark A Shabman

(57) ABSTRACT

A temperature-rainfall-reservoir water combined testing system for a permafrost landslide model includes a tempered glass case with a permafrost landslide model and reservoir water provided therein; a temperature control system provided on the tempered glass case and including an incubator temperature control module, a landslide mass rear edge water tank temperature control module and an air circulation temperature control module; a seepage control system configured to realize seepage of the permafrost landslide model, and form the reservoir water in front of a landslide mass; a rainfall control system including a water tube, a flow controller and a nozzle, where the nozzle is provided in the tempered glass case, and located above the permafrost landslide model; and a multi-field monitoring system including a temperature sensor, a pore water pressure gauge, a moisture meter and a grating strain gauge that are provided in the permafrost landslide model.

9 Claims, 4 Drawing Sheets

TEMPERATURE-RAINFALL-RESERVOIR WATER COMBINED TESTING SYSTEM AND METHOD FOR PERMAFROST LANDSLIDE MODEL

TECHNICAL FIELD

The present disclosure relates to the technical field of physical methods for measuring and testing ground materials, and in particular to a temperature-rainfall-reservoir water combined testing system and method for a permafrost landslide model.

BACKGROUND

As a four-phase mixture composed of soil-rock particles, ice, water and air, permafrost exists in a negative temperature environment for at least two years. Due to the unstable ice in the permafrost, physical and mechanical properties of the permafrost become unstable extremely with the change of external environments such as temperature rises, rainfalls and seepages.

Under the circumstance of global warming, a series of geological disasters arising from the special permafrost, including landslides and mudslides, are coming one after another. This poses a serious threat to engineering construction in permafrost regions, and causes unpredictable damages to quality development of the engineering construction, people's lives and properties, economic development, etc. Hence, it is significant to research physical tests of permafrost landslides, thereby revealing formation mechanisms and evolution rules of the permafrost landslides, and taking targeted preventive measures.

At present, thanks to disastrous mechanisms researched by worldwide scholars on the permafrost landslides, a good foundation is laid to further research the evolution rules and preventive measures of the permafrost landslides. However, due to special physical and mechanical properties and complex multi-field coupling effects of the permafrost landslides, as well as extreme weather conditions and seasonal changes of the permafrost regions, a lot of more complex and critical problems are still to be solved urgently. Regarding the landslide tests, there have been numerous devices designed by the domestic and foreign scholars. Nevertheless, considerations are rarely given to a model testing device under a temperature, seepage and reservoir water.

SUMMARY OF PRESENT INVENTION

In view of this, embodiments of the present disclosure provide a temperature-rainfall-reservoir water combined testing system and method for a permafrost landslide model. The present disclosure realizes model testing research on a whole process of stabilization, deformation, landslide initiation and instability failure of a permafrost landslide in different temperature and seepage conditions, and monitors multi-field information of a permafrost landslide model in a whole evolution process, thereby deepening the understanding on a seepage-induced mechanism of the permafrost landslide, and providing a test support for construction of a permafrost landslide initiation model.

An embodiment of the present disclosure provides a temperature-rainfall-reservoir water combined testing system for a permafrost landslide model, including:

a tempered glass case, where a permafrost landslide model and reservoir water are provided in the tempered glass case, a water outlet is formed at a bottom of the tempered glass case, a flowmeter is provided at the water outlet, the flowmeter is connected to a measuring instrument, and a tracer is provided in the permafrost landslide model;

a temperature control system provided on the tempered glass case, where the temperature control system includes an incubator temperature control module, a landslide mass rear edge water tank temperature control module and an air circulation temperature control module, and is configured to control a temperature in the tempered glass case;

a seepage control system configured to realize seepage of the permafrost landslide model, and form the reservoir water in front of a landslide mass;

a rainfall control system including a water tube, a flow controller and a nozzle, where the nozzle is provided in the tempered glass case, and located above the permafrost landslide model; the water tube includes one end connected to the nozzle, and the other end connected to a water source, and the flow controller is provided at a connector between the water tube and the nozzle, and configured to control a flow rate of water; and a multi-field monitoring system including a temperature sensor, a pore water pressure gauge, a moisture meter and a grating strain gauge that are provided in the permafrost landslide model and respectively configured to monitor a temperature change, a pore water pressure change, a moisture content and a deformation amount in the permafrost landslide model.

In one embodiment, the landslide mass rear edge water tank temperature control module includes a heating tube and a landslide mass rear edge water tank; and the heating tube is provided in the landslide mass rear edge water tank, and configured to heat water in the landslide mass rear edge water tank.

In one embodiment, a plurality of air inlets and exhaust holes are formed in the tempered glass case; the air circulation temperature control module includes a plurality of air circulation fans; and the air circulation fans are respectively provided at the air inlets.

In one embodiment, an area of the air inlet is greater than an area of the exhaust hole.

In one embodiment, a front sidewall and a top wall of the tempered glass case are transparent; a left sidewall of the tempered glass case is a pull-out glass plate; the exhaust hole is formed in a right sidewall and a rear sidewall of the tempered glass case; and the air circulation fan is provided on the top wall, the front sidewall and the rear sidewall of the tempered glass case.

In one embodiment, the seepage control system includes a constant-flux pump and a pull-out water tank that are provided at a rear edge of the landslide mass; a clapboard is provided in the pull-out water tank, so as to divide the pull-out water tank into a groove A and a groove B; the clapboard is lower than the pull-out water tank; a water inlet tube of the constant-flux pump communicates with the landslide mass rear edge water tank; a water drainage tube of the constant-flux pump communicates with the groove A; and the groove B communicates with the landslide mass rear edge water tank through a connecting tube, so as to realize circulation of heated water.

In one embodiment, the multi-field monitoring system further includes a camera provided above the landslide mass of the permafrost landslide model; and a thermal infrared imager and a three-dimensional (3D) laser scanner are provided at a surface of the landslide mass of the permafrost landslide model.

In one embodiment, the permafrost landslide model includes a crushed ice containing permafrost landslide model and a block ice containing permafrost landslide model.

The present disclosure further provides a temperature-rainfall-reservoir water combined testing method for a permafrost landslide model, which uses the temperature-rainfall-reservoir water combined testing system for a permafrost landslide model, and including the following steps:

- S1, acquiring a composition and a physical property of natural permafrost, performing computer tomography (CT) scanning on a permafrost sample of a research region to obtain a physical structural characteristic of the natural permafrost, and obtaining the composition and a particle grading curve of the natural permafrost through an instrument and a screen test;
- S2, analyzing a structure and a component of the permafrost, preparing remolded permafrost, and providing crushed ice and block ice having different initial ice contents;
- S3, adding the tracer having a certain concentration to an ice preparing solution, and monitoring a flow rate at a downstream seepage water outlet of the landslide mass and the concentration of the tracer, so as to monitor an ice thawing amount in the permafrost landslide model in real time, where the measuring instrument at the water outlet monitors the concentration of the tracer in water in real time;
- S4, fully mixing the remolded permafrost with the crushed ice and the block ice having the different initial ice contents respectively to obtain the crushed ice containing permafrost landslide model and the block ice containing permafrost landslide model;
- S5, providing, when preparing the permafrost landslide model, a plurality of monitoring instruments such as the temperature sensor, the pore water pressure gauge, the moisture meter, the grating strain gauge and a flexible displacement meter in the landslide model, where the temperature sensor is configured to monitor a temperature field; the pore water pressure gauge is configured to monitor a seepage field; the grating strain gauge and the flexible displacement meter are configured to monitor a deformation field, and the moisture meter is configured to monitor the seepage field;
- S6, putting the permafrost landslide model into the tempered glass case, adjusting an arrangement position of each of the monitoring instruments, and guaranteeing normal use of the instrument;
- S7, designing a temperature rise amplitude and a temperature rise rate in different working conditions, and debugging the incubator temperature control module and the landslide mass rear edge water tank temperature control module, such that the tempered glass case is located in a relatively stable temperature environment;
- S8, designing a seepage gradient in the different working conditions, pumping heated water to the pull-out water tank through the constant-flux pump, and debugging a water level in the tempered glass case, thereby ensuring that seepage is formed in the model and the reservoir water is formed at a front edge of the landslide mass, and the flowmeter monitors and records a change of the flow rate in real time;
- S9, providing the flow controller to control a rainfall intensity, and debugging a spraying direction and a covering range of the nozzle; and
- S10, connecting and debugging the high-speed camera, the thermal infrared imager and the 3D laser scanner, testing the crushed ice containing permafrost landslide model and the block ice containing permafrost landslide model in multiple different working conditions through a control variate method, and allowing each instrument to monitor and record data in real time.

The technical solutions provided by the embodiments of the present disclosure achieve the following beneficial effects: The temperature-rainfall-reservoir water combined testing system for a permafrost landslide model can realize model testing research on a whole process of stabilization, deformation, landslide initiation and instability failure of a permafrost landslide in different temperature, rainfall and reservoir water conditions. By developing a series of whole-process evolution tests of the permafrost landslide model in different ice occurrence forms, initial ice contents, temperature rise rates and amplitudes, seepage gradients and rainfall intensities, the present disclosure obtains multi-field monitoring time series data of the permafrost landslide, and deformation and destruction characteristics of the landslide in the whole evolution process, thereby analyzing a multi-field linkage mechanism and a multi-field spatio-temporal evolution rule of the permafrost landslide in temperature rises.

In the figures: 1—permafrost landslide model, 2—thermal infrared imager, 3—flowmeter, 4—3D laser scanner, 5—tempered glass case, 6—data acquisition instrument, 7—camera, 8—air circulation fan, 9—landslide mass rear edge water tank temperature control module, 10—moisture meter, 11—grating strain gauge, 12—flexible displacement meter, 13—temperature sensor, 14—pore water pressure gauge, 15—nozzle, 16—rainfall hole, 17—water tube, 18—flow controller, 19—constant-flux pump, 20—water inlet tube, 21—water drainage tube, 22—groove B, 23—connecting tube, 24—groove A, 25—pull-out water tank, 26—landslide mass rear edge water tank, 27—heating tube, 28—clapboard, 29—exhaust hole, 30—reservoir water, and 31—measuring instrument.

DETAILED DESCRIPTION OF THE EMBODIMENTS

In order to make the objective, technical solution and advantages of the present disclosure clearer, embodiments of the present disclosure will be further described in detail in conjunction with the accompanying drawings.

Figure 1:
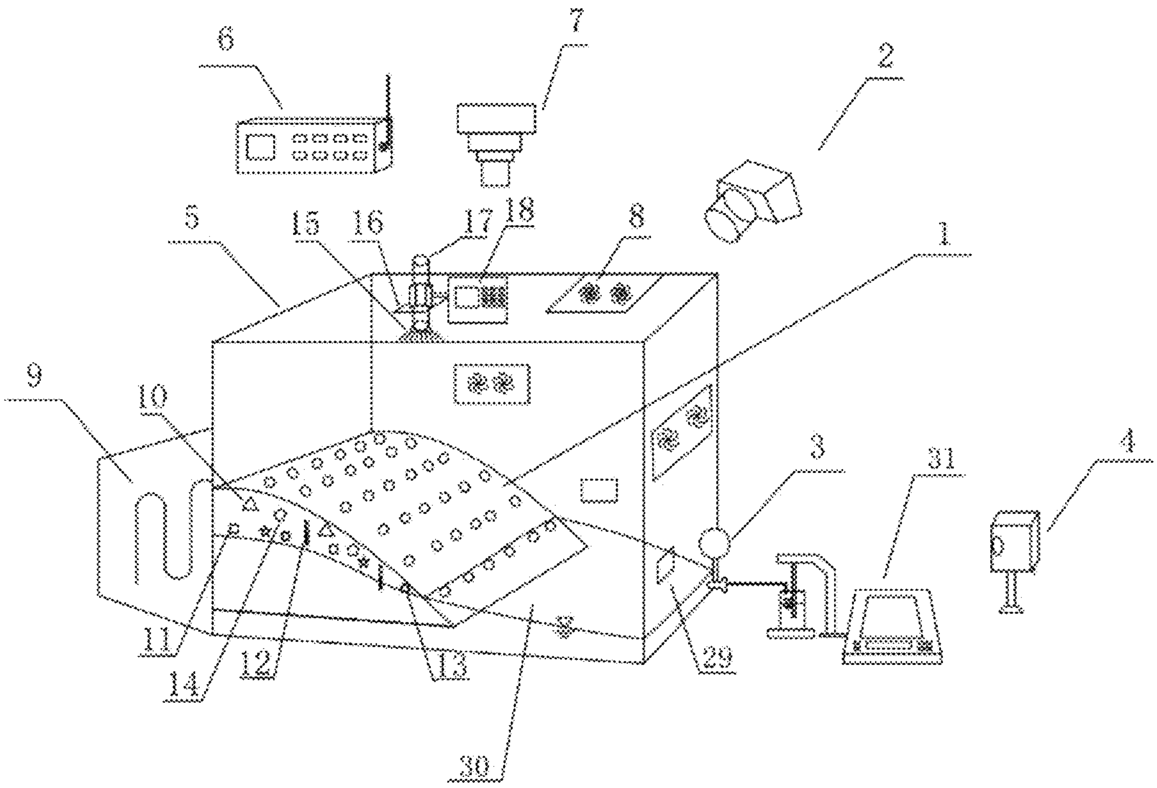
FIG. 1 is a schematic structural view of a temperature-rainfall-reservoir water combined testing system for a permafrost landslide model according to an embodiment of the present disclosure.
Figure 2:
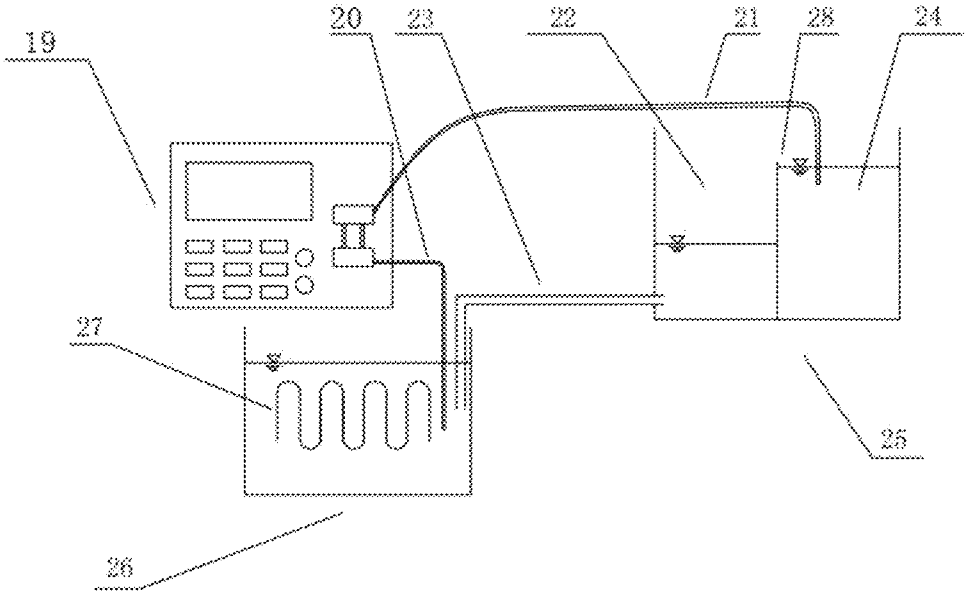
FIG. 2 is a schematic view of a landslide mass rear edge water tank temperature control module in FIG. 1.
Figure 3:
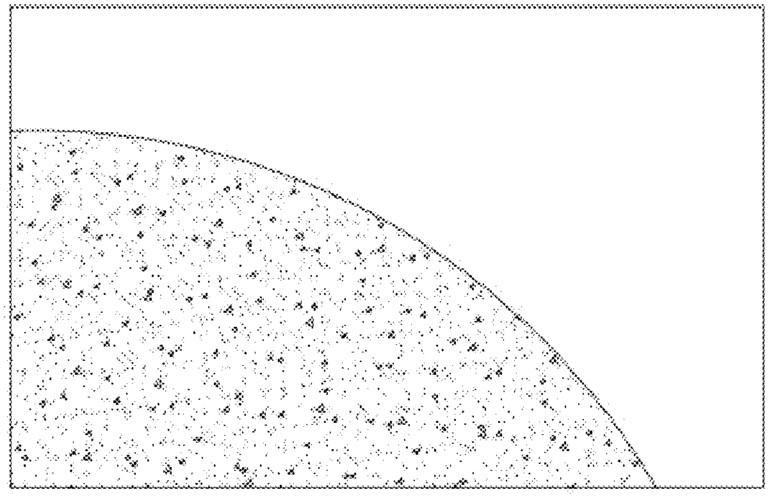
FIG. 3 illustrates a crushed ice containing permafrost landslide model.
Figure 4:
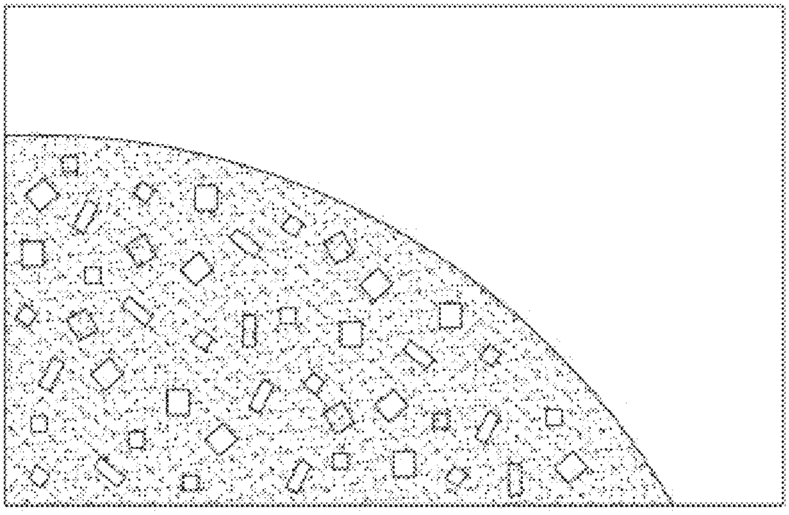
FIG. 4 illustrates a block ice containing permafrost landslide model.

Referring to FIG. 1 to FIG. 4, an embodiment of the present disclosure provides a temperature-rainfall-reservoir water 30 combined permafrost landslide model 1 testing system, including a tempered glass case 5, a temperature control system, a seepage control system, a rainfall control system and a multi-field monitoring system. A permafrost landslide model 1 and reservoir water 30 are provided in the tempered glass case 5 to form a model case. A water outlet is formed at a bottom of the tempered glass case 5. A flowmeter 3 is provided at the water outlet. The flowmeter 3 is connected to a measuring instrument 31. A tracer is provided in the permafrost landslide model 1. With the tracer, an ice thawing amount in the permafrost landslide model 1 can be monitored in real time. The tracer having a certain concentration, such as a sodium chloride experimental solution and a carmine experimental solution, is added to an ice preparing solution. By monitoring a flow rate at the downstream seepage outlet of a landslide mass and the concentration of the tracer, the ice thawing amount is monitored in real time.

The temperature control system is provided on the tempered glass case 5. The temperature control system includes an incubator temperature control module, a landslide mass rear edge water tank temperature control module 9 and an air circulation temperature control module, and is configured to control a temperature in the tempered glass case 5. Specifically, the incubator temperature control module can provide a long-time and stable temperature environment for the whole model case in a range of −20° C. to 50° C., and has a constant temperature rise and fall function. According to an experimental requirement, the incubator temperature control module can adjust the appropriate temperature environment for the model case. The landslide mass rear edge water tank temperature control module 9 includes a heating tube 27 and a landslide mass rear edge water tank 26. The heating tube 27 is provided in the landslide mass rear edge water tank 26, and configured to heat water in the landslide mass rear edge water tank 26. The heating tube 27 can stabilize a temperature of the water in the rear edge water tank at a certain value for a long time in a range of 2° C. to 30° C., and also has a constant temperature rise and fall function.

The seepage control system is configured to realize seepage of the permafrost landslide model 1, and form the reservoir water 30 in front of the landslide mass. The seepage control system can control a water level in the water tank at a preset height, has a constant water level rise and fall function, and can be provided with different seepage gradients according to an experimental requirement.

The rainfall control system includes a water tube 17, a flow controller 18 and a nozzle 15. The nozzle 15 is provided in the tempered glass case 5, and located above the permafrost landslide model 1. Herein, a rainfall hole 16 may be formed in a top wall of the tempered glass case 5. The water tube 17 includes one end connected to the nozzle 15, and the other end connected to a water source. The flow controller 18 is provided at a connector between the water tube 17 and the nozzle 15, and configured to control a flow rate of water. The flow controller 18 has different flow gradients, and can simulate and control a rainfall intensity. The nozzle 15 can change a spraying direction and a spraying range. It sprays water uniformly to a surface of the permafrost landslide model 1 to simulate different rainfall conditions.

The multi-field monitoring system includes a temperature sensor 13, a pore water pressure gauge 14, a moisture meter 10 and a grating strain gauge 11 that are provided in the permafrost landslide model 1 and respectively configured to monitor a temperature change, a pore water pressure change, a moisture content and a deformation amount in the permafrost landslide model 1. The temperature sensor 13 can sense a temperature change of the permafrost landslide model 1 in real time and output the temperature change as stable data, and can be configured to monitor a temperature field. The pore water pressure gauge 14 can measure a change of a pore water pressure of the permafrost landslide model 1 in different temperature gradients and different seepage gradients, and is configured to monitor a seepage field. The grating strain gauge 11 is mainly configured to measure a strain and a deformation of the model, and monitor a deformation field.

Specifically, a plurality of air inlets and exhaust holes 29 are formed in the tempered glass case 5. The air circulation temperature control module includes a plurality of air circulation fans 8. The air circulation fans 8 are respectively provided at the air inlets. With a dynamic design of an aircraft turbine, the air circulation fan 8 can realize circulated wind discharge. Strong spiral wind can quickly push air in the model case to circulate and flow, thereby changing a temperature of a soil layer on the surface of the permafrost landslide model. Meanwhile, by changing an air speed of the air circulation fan 8, impacts of the air temperature on the soil at different air speeds can be realized. The exhaust hole 29 can balance an air pressure in the model case.

Preferably, an area of the air inlet is greater than an area of the exhaust hole 29. This facilitates air circulation, and makes the temperature in the model case more uniform.

Specifically, in the embodiment, the tempered model case is a multilayer vacuum transparent tempered glass case 5, and is made of transparent tempered glass. A front sidewall and a top wall of the tempered glass case are transparent. A left sidewall of the tempered glass case is a pull-out glass plate. The exhaust hole 29 is formed in a right sidewall and a rear sidewall of the tempered glass case. The air circulation fan is provided on the top wall, the front sidewall and the rear sidewall of the tempered glass case. The glass case can make a test process visual, such that a whole evolution process of stabilization, deformation, landslide initiation and instability failure of a permafrost landslide in different temperature and seepage conditions is observed in real time. Moreover, the glass case can isolate heat exchange of the whole permafrost landslide model 1 testing system with the outside, such that the model case is located in the stable temperature environment.

Specifically, the seepage control system includes a constant-flux pump 19 and a pull-out water tank 25 that are provided at a rear edge of the landslide mass. A clapboard 28 is provided in the pull-out water tank 25, so as to divide the pull-out water tank 25 into a groove A 24 and a groove B 22. The clapboard 28 is lower than the pull-out water tank 25. A water inlet tube 20 of the constant-flux pump 19 communicates with the landslide mass rear edge water tank 26. A water drainage tube 21 of the constant-flux pump 19 communicates with the groove A 24. The groove B 22 communicates with the landslide mass rear edge water tank 26 through a connecting tube 23, so as to realize circulation of heated water. The groove A 24 can provide different seepage conditions for the permafrost landslide model 1, while the groove B 22 collects overflowed water and makes the water enter the landslide mass rear edge water tank 26 through the connecting tube 23, thereby realizing circulation of heated water. The constant-flux pump 19 can pump the heated water to the pull-out water tank 25 continuously, thereby realizing the seepage of the permafrost landslide model 1, and forming the reservoir water 30 at a front edge of the landslide mass. The flowmeter 3 connected to the water outlet of the model case can monitor a flow rate of water from the model case in real time. The measuring instrument 31 connected to the flowmeter 3 can monitor the concentration of the tracer in the water in real time, thereby monitoring the ice thawing amount in the landslide model.

Further, the multi-field monitoring system further includes a camera 7 provided above the landslide mass of the permafrost landslide model 1. A thermal infrared imager 2 and a 3D laser scanner 4 are provided at a surface of the landslide mass of the permafrost landslide model 1. The camera 7 is the high-speed camera 7. With an acA4112-8gc type, the camera is configured to record a whole destruction process of the landslide mass. The thermal infrared imager 2 is the Xinfrared-T3Pro thermal infrared imager 2. The 3D laser scanner 4 is the Optech Polaris LR 3D laser scanner 4, and is configured to acquire temperature information and deformation information on the surface of the landslide surface of the landslide model in the whole evolution process. The thermal infrared imager 2 may be configured to monitor the temperature field, and the 3D laser scanner 4 may be configured to monitor the deformation field.

Specifically, the permafrost landslide model 1 includes a crushed ice containing permafrost landslide model 1 and a block ice containing permafrost landslide model 1. During manufacture, crushed ice and block ice may be used respectively, and fully mixed with a remolded permafrost sample, thereby obtaining the crushed ice containing permafrost landslide model 1 and the block ice containing permafrost landslide model 1.

It is to be noted that a data acquisition instrument 6 connected to various instruments to acquire and summarize measurement data is further provided outside the tempered glass case 5.

The present disclosure further provides a temperature-rainfall-reservoir water 30 combined permafrost landslide model 1 testing method, which uses the temperature-rainfall-reservoir water 30 combined permafrost landslide model 1 testing system, and includes the following steps:

In S1, a composition and a physical property of natural permafrost are acquired. CT scanning is performed on a permafrost sample of a research region to obtain a physical structural characteristic of the natural permafrost. The composition and a particle grading curve of the natural permafrost are obtained through an instrument and a screen test.

In S2, a structure and a component of the permafrost are analyzed. Remolded permafrost is prepared. Crushed ice and block ice having different initial ice contents are provided.

In S3, the tracer having a certain concentration is added to an ice preparing solution, and a flow rate at a downstream seepage water outlet of the landslide mass and the concentration of the tracer is monitored, so as to monitor an ice thawing amount in the permafrost landslide model 1 in real time. The measuring instrument 31 at the water outlet monitors the concentration of the tracer in water in real time.

In S4, the remolded permafrost is fully mixed with the crushed ice and the block ice having the different initial ice contents respectively to obtain the crushed ice containing permafrost landslide model 1 and the block ice containing permafrost landslide model 1. Each model includes multiple working conditions.

In S5, when the permafrost landslide model 1 is prepared, a plurality of monitoring instruments such as the temperature sensor 13, the pore water pressure gauge 14, the moisture meter 10, the grating strain gauge 11 and a flexible displacement meter 12 are provided in the landslide model. The temperature sensor 13 is configured to monitor a temperature field. The pore water pressure gauge 14 is configured to monitor a seepage field. The grating strain gauge 11 and the flexible displacement meter 12 are configured to monitor a deformation field. The moisture meter 10 is configured to monitor the seepage field.

In S6, the permafrost landslide model 1 is put into the tempered glass case 5. An arrangement position of each of the monitoring instruments is adjusted, and normal use of the instrument is guaranteed.

In S7, a temperature rise amplitude and a temperature rise rate in different working conditions are designed. The incubator temperature control module and the landslide mass rear edge water tank temperature control module 9 are debugged, such that the tempered glass case 5 is located in a relatively stable temperature environment.

In S8, a seepage gradient in the different working conditions is designed. Heated water is pumped to the pull-out water tank 25 through the constant-flux pump 19. A water level in a model case is debugged, thereby ensuring that seepage is formed in the model and the reservoir water 30 is formed at a front edge of the landslide mass, and the flowmeter 3 monitors and records a change of the flow rate in real time.

In this step, after the water level in the pull-out water tank 25 reaches a certain height, a right plate in the groove A of the pull-out water tank 25 and a left glass plate of the transparent tempered glass case 5 are pulled out at the same time, thereby realizing a seepage working condition, and ensuring that the seepage is formed in the model and the reservoir water 30 is formed at the front edge of the landslide mass. Meanwhile, water overflowed out of the clapboard 28 enters the groove B 22. The water enters the landslide mass rear edge water tank 26 through the connecting tube 23, thereby realizing circulation of the heated water. The flowmeter 3 monitors and records the change of the flow rate in real time.

In S9, the flow controller 18 is provided to control a rainfall intensity. A spraying direction and a covering range of the nozzle 15 are debugged.

In S10, the high-speed camera 7, the thermal infrared imager 2 and the 3D laser scanner 4 are connected and debugged. The crushed ice containing permafrost landslide model 1 and the block ice containing permafrost landslide model 1 are tested in multiple different working conditions through a control variate method. Each instrument monitors and records data in real time.

The present disclosure has the following beneficial effects:

(1) According to the present disclosure, the temperature control system includes an incubator temperature control module, a landslide mass rear edge water tank temperature control module 9 and an air circulation temperature control module. With the three modules, the present disclosure can realize evolution of the ice-containing permafrost in multiple working conditions, such as different temperatures and different temperature rise rates. With a dynamic design of an aircraft turbine, the air circulation fan 8 in the air circulation temperature control module can realize circulated wind discharge. Strong spiral wind can quickly push air in the model case to circulate and flow, thereby changing a temperature of a soil layer on the surface of the permafrost landslide model 1. Meanwhile, by changing an air speed of the air circulation fan 8, impacts of the air temperature on the soil at different air speeds can be realized. An area of the air inlet at the air circulation fan 8 is greater than an area of the exhaust hole 29. This facilitates air circulation, and makes the temperature in the model case more uniform.

(2) In the seepage control system, heated water is pumped to the pull-out water tank 25 through the constant-flux pump 19. The water tank is divided into the groove A and the groove B 22. The water in the groove A 24 can realize different seepage working conditions for the permafrost landslide model 1, while the groove B 22 collects overflowed water and makes the water enter the landslide mass rear edge water tank 26 through the connecting tube 23, thereby realizing circulation of the heated water. The flowmeter 3 connected to the water outlet of the model case can monitor a flow rate of water from the model case in real time.

(3) In the rainfall control system, the flow controller 18 can adjust the rainfall intensity, and the nozzle 15 can change the spraying direction and the covering range, so as to better simulate natural condition.

(4) The tracer having a certain concentration is added to the ice preparing solution. By monitoring the flow rate at the downstream seepage outlet of the landslide mass and the concentration of the tracer, the ice thawing amount is monitored in real time.

(5) The high-speed camera 7 is provided above the permafrost landslide mass, and configured to record a whole destruction process of the landslide mass. The thermal infrared imager 2 and the 3D laser scanner 4 are provided at a surface of the landslide mass, and is configured to acquire temperature information and deformation information on the surface of the landslide mass of the landslide model in the whole evolution process.

Herein, the involved orientation terms such as "front", "rear", "upper", and "lower" are defined in terms of the positions of parts and between the parts in the drawings, which are used just for clarity and convenience of expressing the technical solution. It should be understood that the use of such orientation terms should not limit the protection scope claimed by the present disclosure.

The above embodiments and the features of the embodiments herein may be combined with each other without conflict.

The above are merely preferred examples of the present disclosure, and are not intended to limit the present disclosure. Any modifications, equivalent replacements, improvements, and the like made within the spirit and principle of the present disclosure shall be all included in the protection scope of the present disclosure.

What is claimed is:

1. A temperature-rainfall-reservoir water combined testing system for a permafrost landslide model, comprising:

a tempered glass case, wherein a permafrost landslide model and reservoir water are provided in the tempered glass case, a water outlet is formed at a bottom of the tempered glass case, a flowmeter is provided at the water outlet, the flowmeter is connected to a measuring instrument, and a tracer is provided in the permafrost landslide model;

a temperature control system provided on the tempered glass case, wherein the temperature control system comprises an incubator temperature control module, a landslide mass rear edge water tank temperature control module and an air circulation temperature control module, and the incubator temperature control module and the air circulation temperature control module are configured to control a temperature in the tempered glass case;

a seepage control system configured to realize seepage of the permafrost landslide model, and form the reservoir water in front of a landslide mass;

a rainfall control system comprising a water tube, a flow controller and a nozzle, wherein the nozzle is provided in the tempered glass case, and located above the permafrost landslide model; the water tube comprises one end connected to the nozzle, and the other end connected to a water source; and the flow controller is provided at a connector between the water tube and the nozzle, and configured to control a flow rate of water; and a multi-field monitoring system comprising a temperature sensor, a pore water pressure gauge, a moisture meter and a grating strain gauge that are provided in the permafrost landslide model and respectively configured to monitor a temperature change, a pore water pressure change of the permafrost landslide model itself, a moisture content and a deformation amount in the permafrost landslide model.

2. The temperature-rainfall-reservoir water combined testing system according to claim 1, wherein the landslide mass rear edge water tank temperature control module comprises a heating tube and a landslide mass rear edge water tank; and the heating tube is provided in the landslide mass rear edge water tank, and configured to heat water in the landslide mass rear edge water tank.

3. The temperature-rainfall-reservoir water combined testing system according to claim 2, wherein a plurality of air inlets and exhaust holes are formed in the tempered glass case; the air circulation temperature control module comprises a plurality of air circulation fans; and the air circulation fans are respectively provided at the air inlets.

4. The temperature-rainfall-reservoir water combined testing system according to claim 3, wherein an area of the air inlet is greater than an area of the exhaust hole.

5. The temperature-rainfall-reservoir water combined testing system according to claim 3, wherein a front sidewall and a top wall of the tempered glass case are transparent; a left sidewall of the tempered glass case is a pull-out glass plate; the exhaust holes are formed in a right sidewall and a rear sidewall of the tempered glass case; and the air circulation fans are provided on the top wall, the front sidewall and the rear sidewall of the tempered glass case.

6. The temperature-rainfall-reservoir water combined testing system according to claim 2, wherein the seepage control system comprises a constant-flux pump and a pull-out water tank that are provided at a rear edge of the landslide mass; a clapboard is provided in the pull-out water tank, so as to divide the pull-out water tank into a groove A and a groove B; the clapboard is lower than the pull-out water tank; a water inlet tube of the constant-flux pump communicates with the landslide mass rear edge water tank; a water drainage tube of the constant-flux pump communicates with the groove A; and the groove B communicates with the landslide mass rear edge water tank through a connecting tube, so as to realize circulation of heated water.

7. The temperature-rainfall-reservoir water combined testing system according to claim 6, wherein the multi-field monitoring system further comprises a camera provided above the landslide mass of the permafrost landslide model; and a thermal infrared imager and a three-dimensional (3D) laser scanner are provided at a surface of the landslide mass of the permafrost landslide model.

8. A temperature-rainfall-reservoir water combined testing method for a permafrost landslide model, using the temperature-rainfall-reservoir water combined testing system according to claim 7, and comprising the following steps:

S1, acquiring a composition and a physical property of natural permafrost, performing computer tomography (CT) scanning on a permafrost sample of a research region to obtain a physical structural characteristic of the natural permafrost, and obtaining the composition and a particle grading curve of the natural permafrost through an instrument and a screen test;

S2, analyzing a structure and a component of the permafrost, preparing remolded permafrost, and providing crushed ice and block ice having different initial ice contents;

S3, adding the tracer having a certain concentration to an ice preparing solution, and monitoring a flow rate at a downstream seepage water outlet of the landslide mass and the concentration of the tracer, so as to monitor an ice thawing amount in the permafrost landslide model in real time, wherein the measuring instrument at the water outlet monitors the concentration of the tracer in water in real time;

S4, fully mixing the remolded permafrost with the crushed ice and the block ice having the different initial ice contents respectively to obtain the crushed ice containing permafrost landslide model and the block ice containing permafrost landslide model;

S5, providing, when preparing the permafrost landslide model, a plurality of monitoring instruments comprising the temperature sensor, the pore water pressure gauge, the moisture meter, the grating strain gauge and a flexible displacement meter in the landslide model, wherein the temperature sensor is configured to monitor a temperature field; the pore water pressure gauge is configured to monitor a seepage field; the grating strain gauge and the flexible displacement meter are configured to monitor a deformation field, and the moisture meter is configured to monitor the seepage field;

S6, putting the permafrost landslide model into the tempered glass case, adjusting an arrangement position of each of the monitoring instruments;

S7, designing a temperature rise amplitude and a temperature rise rate in different working conditions, and calculating the incubator temperature control module and the landslide mass rear edge water tank temperature control module;

S8, designing a seepage gradient in the different working conditions, pumping heated water to the pull-out water tank through the constant-flux pump, and debugging a water level in the tempered glass case, thereby ensuring that seepage is formed in the model and the reservoir water is formed at a front edge of the landslide mass, and the flowmeter monitors and records a change of the flow rate in real time;

S9, providing the flow controller to control a rainfall intensity, and debugging a spraying direction and a covering range of the nozzle; and S10, connecting and debugging the high-speed camera, the thermal infrared imager and the three-dimensional (3D) laser scanner, testing the crushed ice containing permafrost landslide model and the block ice containing permafrost landslide model in multiple different working conditions through a control variate method, and allowing each instrument to monitor and record data in real time.

9. The temperature-rainfall-reservoir water combined testing system according to claim 1, wherein the permafrost landslide model comprises a crushed ice containing permafrost landslide model and a block ice containing permafrost landslide model.

* * * * *